(12) United States Patent
Bertini et al.

(10) Patent No.: US 12,103,905 B2
(45) Date of Patent: Oct. 1, 2024

(54) UREA PRODUCTION PROCESS AND PLANT

(71) Applicant: Casale SA, Lugano (CH)

(72) Inventors: Paolo Bertini, Lugano (CH); Matteo Fumagalli, San Fermo della Battaglia (IT)

(73) Assignee: Casale SA, Lugano (CH)

( * ) Notice: Subject to any disclaimer, the term of this patent is extended or adjusted under 35 U.S.C. 154(b) by 0 days.

(21) Appl. No.: 18/282,123

(22) PCT Filed: Apr. 5, 2022

(86) PCT No.: PCT/EP2022/058933
§ 371 (c)(1),
(2) Date: Sep. 14, 2023

(87) PCT Pub. No.: WO2022/214453
PCT Pub. Date: Oct. 13, 2022

(65) Prior Publication Data
US 2024/0217924 A1      Jul. 4, 2024

(30) Foreign Application Priority Data
Apr. 7, 2021   (EP) .................................... 21167251

(51) Int. Cl.
*C07C 273/04*      (2006.01)
*B01J 19/00*        (2006.01)
(Continued)

(52) U.S. Cl.
CPC ......... *C07C 273/04* (2013.01); *B01J 19/0013* (2013.01); *B01J 19/1875* (2013.01);
(Continued)

(58) Field of Classification Search
None
See application file for complete search history.

(56) References Cited

U.S. PATENT DOCUMENTS

2015/0133690 A1\* 5/2015 Mennen ................... B01J 10/00
                                                                    422/187
2016/0362360 A1    12/2016 Mennen et al.

FOREIGN PATENT DOCUMENTS

EP       2844640  A1    11/2015
EP       3020702  A1     5/2016
(Continued)

OTHER PUBLICATIONS

International Search Report issued Jul. 22, 2022 in connection with PCT Application No. PCT/EP2022/058933.
(Continued)

*Primary Examiner* — Sudhakar Katakam
*Assistant Examiner* — Jennifer C Sawyer
(74) *Attorney, Agent, or Firm* — Akerman LLP

(57) ABSTRACT

Process for the preparation of urea granules comprising the steps of obtaining an aqueous urea solution from one or more synthesis and recovery steps wherein ammonia and carbon dioxide are reacted together, subjecting the aqueous urea solution to an evaporation step wherein water is removed to obtain a urea melt (1), processing and treating said urea melt in a granulation step (7) and optionally in a cooling section (10) to obtain solid urea granules (14); the process further comprises a scrubbing step (3) of granulation offgas and an atmospheric evaporation step (32) to recover a urea solution (2) and a water-saturated air stream (18): the water-saturated air stream is fed back to the scrubbing section (3) without condensation, and the recovered urea solution is conveyed to the granulation step (7).

14 Claims, 1 Drawing Sheet

(51) Int. Cl.
*B01J 19/18* (2006.01)
*C07C 273/16* (2006.01)
(52) U.S. Cl.
CPC ... *C07C 273/16* (2013.01); *B01J 2219/00024* (2013.01); *B01J 2219/00092* (2013.01)

(56) References Cited

FOREIGN PATENT DOCUMENTS

| EP | 2844640 B1 | 8/2018 |
|----|------------|--------|
| WO | 2013/165245 A1 | 11/2013 |

OTHER PUBLICATIONS

Written Opinion of the International Searching Authority issued Jul. 22, 2022 in connection with PCT Application No. PCT/EP2022/058933.

International Preliminary Report on Patentability issued Feb. 28, 2023 in connection with PCT Application No. PCT/EP2022/058933.

\* cited by examiner

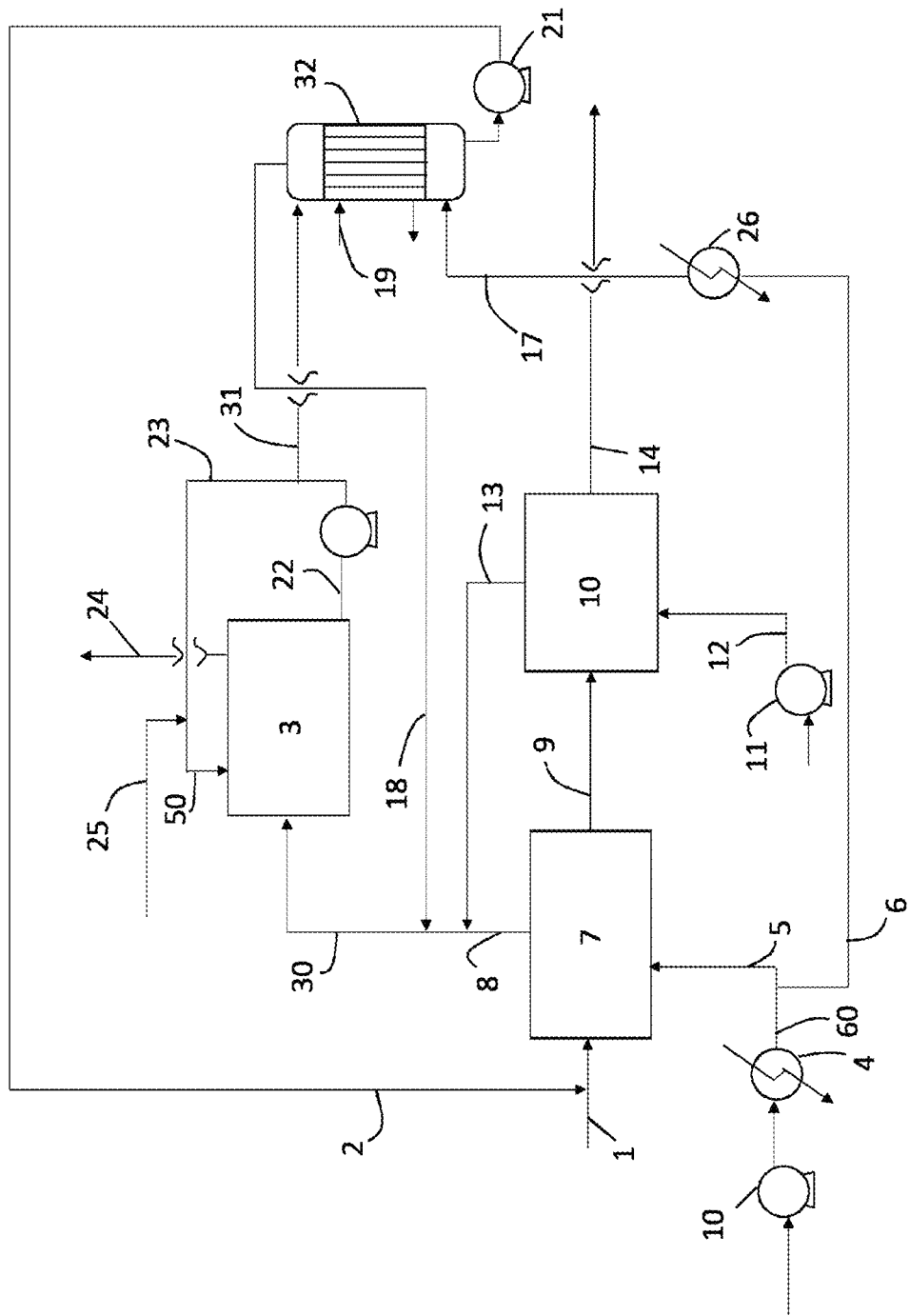

UREA PRODUCTION PROCESS AND PLANT

CROSS-REFERENCE TO RELATED APPLICATIONS

This application is a national phase of PCT/EP2022/058933, filed Apr. 5, 2022, and claims priority to EP 21167251.4, filed Apr. 7, 2021, the entire contents of both of which are hereby incorporated by reference.

FIELD OF APPLICATION

The invention is in the field of urea production, and particularly pertains to the production of solid urea particles. The invention particularly pertains to reducing the energy consumption in such a process. The invention also pertains to a urea production plant and to a revamping method of an existing urea production plant.

PRIOR ART

Urea is synthesised by reacting ammonia and carbon dioxide at high temperature and pressure. An overview of the industrial synthesis of urea can be found in the Ullmann's Encyclopedia of industrial Chemistry, Wiley-VCH Verlag.

Typically, a urea plant comprises a high-pressure synthesis section where ammonia and carbon dioxide are reacted at high pressure to form a urea-containing aqueous solution, and a recovery section where the effluent of the synthesis section is processed at a lower pressure to recover unconverted reagents contained therein and obtain a solution consisting predominantly of urea and water.

The synthesis section comprises a urea synthesis reactor and may further comprise a stripper and a condenser working at synthesis pressure in a so-called high-pressure synthesis loop.

The recovery section may include one or more stages wherein the urea solution is treated to dissociate ammonium carbamate into ammonia and carbon dioxide, which are removed from the urea solution and condensed to form a recycling solution.

When urea is produced in a solid form, the plant typically comprises a section for vacuum evaporation arranged to remove water from the solution withdrawn from the recovery section and to obtain a highly concentrated urea solution or a urea melt; a water treatment section arranged to process the water removed from the solution; a finishing section arranged to convert the highly concentrated solution or the urea melt into a solid urea product.

The most common finishing processes are granulation and prilling. A suitable additive may be added to the urea melt to improve the finishing process, for example formaldehyde is typically added to increase strength and to act as anticaking agent.

More specifically, in a typical case the synthesis section produces an aqueous solution of urea containing unconverted ammonium and carbon dioxide, which is treated in the recovery section to recover the unconverted reagents in the form of a recycling solution commonly named ammonium carbamate solution, which is recirculated to the synthesis section. A concentrated urea solution obtained in the recovery section is further concentrated in the vacuum evaporator section to get a urea melt or a highly concentrated solution. The finishing section processes said melt or solution to obtain a solid urea product in the form of prills or granules.

The granulation process is preferred due to the superior quality (crushing strength) of granules compared to prills. In a granulation process, the urea melt is solidified in a granulator wherein a bed of granules is maintained in a so-called fluidised state through air currents. A cooler is usually arranged downstream of the granulator wherein the urea granulates are cooled by contact with air or by indirect contact with water.

The air streams that exit the granulator and the cooler are rich in urea powder which cannot be directly vented into the atmosphere due to the limit imposed by the environmental regulations and further in view of its content of valuable urea. In addition, the air extracted from the granulator may be contaminated by additives used in the finishing process.

Hence the granulation process produces a so-called granulation offgas which is typically air (fluidising air and/or cooling air) loaded with urea dust. A granulation process poses the problem of how to process this urea-loaded air withdrawn from the granulator.

Typically, the granulation offgas is treated in a scrubbing section where the urea powder is removed by contact with an aqueous urea solution. Optionally an acid solution (sulfuric or nitric acid-based) is used to scrub the residual ammonia from the granulation offgas so as to comply with the environmental regulations.

A portion of the aqueous urea solution leaving the scrubber is continuously recirculated back to the scrubber with the addition of a water make-up stream to keep the concentration and accumulation of the aqueous urea solution circulating constant.

A second portion of the aqueous urea solution is conversely purged and recovered in the plant, where it is mixed with the urea solution produced from the synthesis and the recovery sections. After mixing, the produced and the recycled urea solutions are then concentrated in a vacuum evaporator and fed to the granulation unit.

The recycled urea solution may contain some contaminants such as formaldehyde, ammonium salts or other substances that may be used as additives during the granulation stage of the urea melt. Such contaminants may cause corrosion issues in the plant when the recycled and the produced urea solution are mixed together, and they may be detrimental to the final quality of the urea product. Typically, high-purity urea is needed for the production of Diesel Exhaust Fluid (DEF) for the treatment of the NOx or for the synthesis of melamine.

The vapour stream originated from the evaporation section, which is normally contaminated with a low amount of $NH_3$ and $CO_2$, is sent to a condensation step, typically using a known vacuum condensation technique to yield an aqueous solution in the condensation section.

The aqueous solution obtained in the condensation section is then fed to a process condensate treatment section, which is typically a deep hydrolysis section, followed by stripping to convert the residual urea and to remove the residual $NH_3$ and $CO_2$. Both the deep hydrolysis and the removal of $NH_3$ and $CO_2$ require valuable steam.

In the art, there is a continuous effort to minimise the amount of steam required for this purpose, and there is a continuous desire to reduce the investment cost of the process condensate purification section.

Aiming at doing so, EP 2 844 640 describes a modified urea synthesis process wherein an additional evaporation loop is added to a conventional urea synthesis process. Said additional evaporation loop comprises an evaporation section and a condensation section communicating respectively with the finishing section and with the scrubbing section of the plant.

This newly modified process reduces energy consumption downstream of the condensation section; however it requires the installation of expensive additional units such as an evaporator provided with a dedicated vacuum system, a condensate collection unit and a circulation loop provided with pumps for circulating the condensate back to the scrubbing section.

Therefore it is still highly desirable to provide an improved urea synthesis process that minimises the amount of water to be treated in the condensation sections of the plant. Additionally, the process should minimise the amount of steam required by the plant (e.g. in the dedicated vacuum system) and should be cost-effective.

SUMMARY OF THE INVENTION

The invention aims to fulfil the above requirements and to overcome the above drawbacks of the prior art.

The aim is reached with a process for the preparation of urea granules according to claim 1.

The process comprises the steps of reacting ammonia and carbon dioxide at urea synthesis pressure to obtain a urea-containing effluent and processing said effluent in at least one recovery step at a lower pressure obtaining an aqueous urea solution; subjecting the aqueous urea solution to an evaporation step wherein water is removed from said aqueous urea solution so as to obtain a urea melt and an aqueous vapour phase; subjecting said urea melt to a granulation step in presence of fluidising air obtaining solid urea granules and a granulation offgas containing air and urea dust; conveying the granulation offgas to a scrubbing step performed with an aqueous scrubbing agent to remove urea dust from the offgas and to produce an aqueous urea solution containing urea removed from the offgas and a purified gaseous stream.

The process further comprises the steps of contacting a first portion of the aqueous urea solution with water to yield said aqueous scrubbing agent, and recirculating said aqueous scrubbing agent to the scrubbing step, feeding a second portion of said aqueous urea solution to a dedicated evaporation step wherein said evaporation step is conducted at atmospheric pressure or below atmospheric pressure, and in presence of an air stream to yield a recovered urea solution and a water-saturated air stream; recirculating the recovered urea solution to the granulation step so that said recovered urea solution is subject to granulation together with the urea melt; recirculating the water-saturated air stream to the scrubbing step without passing through a condensation step, so that said water-saturated air stream is subjected to a scrubbing step together with the granulation offgas.

The evaporation step of said second portion of aqueous solution is preferably carried out at a slightly sub-atmospheric pressure. For example the pressure of this evaporation step may be between the atmospheric pressure and 0.2 bar below atmospheric pressure, more preferably between the atmospheric pressure and 0.1 bar below atmospheric pressure.

A further aspect of the present invention is a urea production plant according to the claims.

The urea production plant comprises a synthesis section configured for the production of an aqueous urea solution from reaction of ammonia and carbon dioxide; a recovery section configured to process the aqueous urea solution effluent from the synthesis section and to recover therefrom unconverted reagents to be sent back to the synthesis section; a first evaporation section configured to obtain a urea melt from a urea solution withdrawn from the recovery section; a finishing section configured to process the urea melt obtained in said first evaporation section and to obtain urea granules, wherein the finishing section comprises at least a granulation section, a scrubbing section and optionally a cooling section, wherein the granulation section is in communication with the scrubbing section via a gas flow line arranged to convey granulation offgas withdrawn from the granulation section into said scrubbing section.

The plant further comprises a second evaporation section, which is placed downstream of the scrubbing section and is separated from said first evaporation section, a line arranged to send a portion of an aqueous urea solution withdrawn from the scrubbing section to the second evaporation section; a line arranged to feed an air stream to the second evaporation section for contact with said portion of aqueous urea solution; a line arranged to send a water saturated air stream withdrawn from the second evaporation section back into the scrubbing section, wherein said second evaporation section is an atmospheric or sub-atmospheric section.

A further aspect of the present invention is a revamping method of a pre-existing urea synthesis plant.

The pre-existing plant, to which the revamping method of the invention is applied, may comprise a synthesis section configured for the production of an aqueous urea solution from reaction of ammonia and carbon dioxide wherein said synthesis section comprises at least a urea reactor; a recovery section configured to process the aqueous urea solution from the synthesis section and to recover therefrom unconverted reagents to be sent back to the synthesis section; a first evaporation section configured to obtain a urea melt from a urea solution withdrawn from the recovery section; wherein said evaporation section comprises at least a vacuum evaporator; a finishing section configured to process said urea melt obtained in said first evaporator section and to obtain a solid urea granulates, wherein said finishing section comprises at least a granulator, a scrubber and optionally a cooler. The synthesis section may comprise, in addition to the urea synthesis reactor, a stripper and a condenser forming a high-pressure synthesis loop. Said loop may also comprise a scrubber to treat the offgas extracted from the reactor and from the condenser. Still further, the method of the present invention is also applicable to urea plants wherein the synthesis section comprises only the urea synthesis reactor.

The method comprises the step of adding a second evaporator, which is an atmospheric or sub-atmospheric evaporator and is arranged downstream of the scrubber, and further adding: a line arranged to send a portion of an aqueous urea solution withdrawn from the scrubber to the second evaporator, a line arranged to feed an air stream to the second evaporator for contact with said portion of aqueous urea solution, a line arranged to send water-saturated air stream withdrawn from the second evaporator back to the scrubber.

With the invention, the urea granulate production capacity of the existing urea plant can be increased meanwhile limiting the cost required for the modifications of the plant and the cost required for the introduction of additional gas/liquid flow lines. Overall, the costs necessary for the plant modification are well compensated by the increased capacity of the plant. Furthermore, no additional vacuum evaporator is required and therefore low steam and low energy consumptions are achieved.

Advantageously, by carrying out the recovery of urea from the granulation offgas in a closed-loop, no recycling of the urea from the finishing section to the concentration and water treatment sections of the plant is necessary. Consequently, the size of the concentration and water treatment sections of the plant can be reduced and even more advantageously, the transfer of contaminants (e.g. formaldehyde) across the plant is avoided.

The additional evaporator introduced after the scrubbing section operates at ambient pressure or close to ambient pressure, therefore a dedicated vacuum system is not required, and a lower steam consumption is envisaged.

The advantages of performing the second evaporation step at or close to atmospheric pressure can be summarized as follows. There is no need of equipment to recover vapours from the concentration of the urea solution, such as ejector, condenser, condensate tank and related recycle pumps; no consumption of steam for the concentration step; the air required by the evaporator can be provided by one of the blowers which feed granulation air to the granulator, without the need of a separate air compressor.

PREFERRED EMBODIMENTS

In the text, the term "fluid communication" refers to any connection between a first part or section of a plant and a second part or section of a plant via which fluids (liquids) or liquids possibly containing some solids, can flow from the first part of the plant to the second part of the plant. Such fluid communication is typically provided by piping systems, hoses, or other devices well-known to the skilled person for the transportation of fluids.

The term "gas flow lines" refers to any connection between a first part or section of a plant and a second part or section of a plant via which gas o vapours possibly retaining some solid particles, can flow from the first part of the plant to the second part of the plant. Such gas flow lines typically comprise piping systems, or other devices well known to the skilled person for the transportation of gases, if needed under above or below atmospheric pressures.

According to a particularly interesting embodiment of the present invention, the process may comprise the steps of subjecting the urea granules exiting the granulator step to a cooling process in presence of cooling air to yield solid urea granules and a cooling off-gas stream and conveying the cooling off-gas stream to the scrubber step together with the granulation offgas and with the water-saturated air stream.

The evaporation step is carried out at or close to atmospheric pressure. In a preferred embodiment, the evaporation step is performed at a pressure between 0 bar rel (i.e. atmospheric pressure) and minus 0.2 bar rel (i.e. 0.2 bar below atmospheric pressure). More preferably the lower limit of the above range is 0.1 bar rel. Advantageously, no vacuum evaporator is required and the consumption of steam is reduced because no vacuum ejectors are required.

Air is fed to the evaporator to lower the partial pressure of water in the vapour phase and therefore promoting the evaporation. The solidification of the urea melt in the granulator is carried out by removing the heat of solidification with fluidising air.

In a preferred embodiment of the invention, the fluidising air fed to the granulation step and the air stream fed to the evaporator are separated from a main collector or a main header that carries a main air stream. Advantageously, said two air streams can share the same air blower unit namely the granulator air blower that is commonly present in conventional urea plants. Advantageously, no additional air blower is required.

According to a preferred embodiment, the air stream fed to the evaporator is subjected to a heating stage before being fed to the evaporation step. Preferably, the temperature of said air stream after the heating stage is in the range of 120 to 170° C., more preferably 130 to 140° C.

Preferably the urea melt produced after the evaporation step and fed to the granulator step contains 95 to 99.7% wt urea or more preferably 95 to 98.8% wt. Said urea melt is solidified in the granulation step and the granulation offgas leaving the granulation stage are then treated in the scrubbing section. Preferably the aqueous urea solution exiting the scrubbing step has a concentration in the range of 40 to 50% wt, more preferably 43 to 47% wt.

According to the invention, the aqueous urea solution leaving the scrubber is partially concentrated in the evaporation step by contacting the aqueous urea solution with an air stream fed to the evaporation step and preferably having a counter-current flow direction with the latter. The recovered urea solution from the evaporation step has a urea concertation preferably in the range of 95 to 98% wt, more preferably of 96% wt or around 96% wt.

Preferably the air stream before being fed to the evaporation step is subjected to a heating stage.

According to a particularly preferred embodiment, the purified gaseous stream exiting the scrubbing section is vented to the atmosphere.

Preferably the heat required for the water evaporation in the evaporation section is provided through steam.

According to a preferred embodiment, the aqueous vapour phase produced in the evaporation stage arranged after the urea synthesis and recovery section is subjected to a condensation step and a process condensation treatment step.

Preferably the process condensation treatment step comprises a deep hydrolysis step and a stripping step to decompose the residual urea and remove $NH_3$ and $CO_2$ that are then recycled to the synthesis and recovery section.

According to the invention, the urea production plant comprises a second evaporation section in fluid communication with the granulation section preferably, the second evaporation section operates at atmospheric pressure.

In an interesting embodiment, the atmospheric evaporator section comprises a falling film evaporator, preferably having a vertical shell-and-tube heat exchanger, with a laterally displaced or concentrically arranged centrifugal separator. Preferably the portion of the aqueous urea solution that is concentrated in the evaporator is supplied to the top of the heating tubes, following a downward direction along the tube walls in the form of a thin film. Preferably, the portion of aqueous urea solution and the air stream are fed to the tubes of the evaporator in counter-current.

Preferably external heating is supplied to the tube with a steam current that pushes the liquid film to boil and to partially evaporate. Air is supplied to reduce the partial pressure of water so to promote the evaporation.

The granulation section comprises at least one granulation unit. The granulation unit is preferably a fluidised bed granulator.

Air can be fed to the granulator section and to the evaporator section respectively via a first line and second gas line. Preferably the first and second gas line are branched off from a main header so that no additional air blower is required. The main header and the first and second gas line may be part of an air supply section of the urea production plant.

In a preferred embodiment, a heat exchanger section is arranged on said second gas line connected to the evaporator section. The heat exchanger section may comprise one or more heat exchangers.

Preferably the air fed to the evaporator is pre-heated to the temperature range of 120 to 170° C., more preferably 130 to 140° ° C. before being fed to the evaporator.

DESCRIPTION OF THE FIGURES

FIG. 1 is a schematic representation of a urea granules production process according to an embodiment of the invention.

DETAILED DESCRIPTION

A urea melt 1 is obtained in a urea plant comprising at least a synthesis section, a recovery section, a section for vacuum evaporation (concentration) and a water treatment section. These sections are of standard design and are well known to the skilled person in the art and for those reasons, are not represented herein. The urea plant producing the melt 1 may be a urea stripping plant.

The urea melt 1 is sent together with a recovered urea solution 2 to a granulator 7 (fluidised bed) wherein the urea melt is solidified in the form of granules 9. The heat of solidification is removed via a fluidising air 5 that leaves the granulator 7 as granulation offgas 8 retaining some urea dust.

Heat is removed in the cooling section 10 from the solidified urea particles 9 in order to cool them to a suitable temperature for safe and conform storage and transport of this final product. Solid urea granules 14, ready for transportation or storage, are extracted from the cooling section 10.

The cooling air 12 supplied by an air blower 11 comes into direct contact with the solidified urea particles in the cooling section 10. Therefore, also the cooling air withdrawn from the cooling section 10 (cooling offgas stream 13) is contaminated with some urea dust.

The granulation offgas 8 and the cooling off-gas stream 13 are sent to a scrubber 3 for removal of the urea dust contained therein. More specifically the granulation offgas 8 and the cooling offgas 13 are mixed with a water-saturated air stream 18 to yield a gas mixture 30. Said water-saturated air stream 18 is extracted from an atmospheric evaporator 32 which will be described below.

The gas mixture 30 is treated in the scrubber 3 with an aqueous scrubbing agent 50 to yield an aqueous urea solution 22 (containing the urea removed from the gas) and a purified gaseous stream 24.

A first portion 23 of the aqueous urea solution 22 is recycled into the scrubber 3 together with a make-up water 25. The recycled solution and the make-up water 25 form the above-mentioned aqueous scrubbing agent 50. The purified gaseous stream 24 may be vented to the atmosphere.

A second portion 31 of the aqueous urea solution 22 is fed to atmospheric or sub-atmospheric evaporator 32 in presence of an air stream 6 to yield a recovered urea solution 2 and a water-saturated air stream 18. The air stream 6 lowers the partial pressure of water in the evaporator 32 and facilitates the evaporation process.

The heat required for the evaporation of water is provided through steam 19.

The evaporator 32 is a shell-and-tube apparatus wherein the evaporation is performed inside the tubes in a falling-film condition. The tubes are externally heated by the steam 19; the solution 31 evaporates while descending in the tubes in counter-current direction with an ascending flow of the air 6.

The recovered urea solution 2 is at a concentration such that it can be directly recirculated back to the granulator via a pump 21 whilst the water-saturated air stream 18 is recirculated back and mixed with the granulation offgas 8 and with the cooling off-gas stream 13.

The air stream 6 is supplied to the evaporator 32 preferably after a pre-heating stage in the heat exchanger 26.

In FIG. 1 it can be appreciated that the line carrying the air stream 6 and the line carrying the fluidising air 5 are branched off from a main collector carrying a main air stream 60 so to limit the number of air blower 10 to just one. Pre-heating of the main air stream is carried out via the heat exchanger 4.

What is claimed is:
1. A process for the preparation of urea granules comprising the steps of:
   a) reacting ammonia and carbon dioxide at urea synthesis pressure to obtain a urea-containing effluent and processing said effluent in at least one recovery step at a lower pressure obtaining an aqueous urea solution;
   b) subjecting the aqueous urea solution to an evaporation step wherein water is removed from said aqueous urea solution so as to obtain a urea melt and an aqueous vapour phase;
   c) subjecting said urea melt to granulation in presence of fluidising air obtaining solid urea granules and a granulation offgas containing air and urea dust;
   d) conveying the granulation offgas to a scrubbing step performed with an aqueous scrubbing agent to remove urea dust from the offgas and to produce an aqueous urea solution containing urea removed from the offgas and a purified gaseous stream;
   e) contacting a first portion of the aqueous urea solution of step (d) with water to yield said aqueous scrubbing agent, and recirculating said aqueous scrubbing agent to the scrubbing step;
   f) feeding a second portion of said aqueous urea solution of step (d) to an evaporation step wherein said evaporation step is conducted in presence of an air stream to yield a recovered urea solution and a water-saturated air stream and wherein said evaporation step is conducted at atmospheric pressure or below atmospheric pressure;
   g) recirculating the recovered urea solution obtained at step (f) to the granulation step so that said recovered urea solution is subject to granulation together with the urea melt;
   h) recirculating the water-saturated air stream to step (d) without passing through a condensation step, so that said water-saturated air stream is subjected to a scrubbing step together with the granulation offgas of step (c).

2. The process according to claim 1, further comprising the step of:
   j) subjecting the urea granules to a cooling process in presence of cooling air to yield solid urea granules and a cooling off-gas stream;
   k) conveying the cooling off-gas stream to the scrubber step together with the granulation offgas and with the water-saturated air stream.

3. The process according to claim 1, wherein the evaporation step according to feature f) is performed at a pressure in the range of 0 bar rel to minus 0.2 bar rel.

4. The process according to claim 1, wherein the fluidising air and the air stream are separated from a main air stream.

5. The process according to claim 1, wherein the aqueous urea solution exiting the scrubbing step has a concentration in the range of 43 to 47% wt.

6. The process according to claim 1, wherein the urea melt of step (b) contains 95 to 99.7% wt urea.

7. The process according to claim 1, wherein the recovered urea solution has a urea concentration in the range of 95 to 98% wt.

8. The process according to claim 1, wherein the air stream is subjected to a heating stage before being fed to the evaporation step.

9. The process according to claim 8, wherein the temperature of the air stream after the heating stage is in the range of 120 to 170° C.

10. The process according to claim 1, wherein the purified gaseous stream is vented to the atmosphere.

11. The process according to claim 3, wherein the evaporation step according to feature f) is performed at a pressure in the range of 0 bar rel to minus 0.1 bar rel.

12. The process according to claim 6, wherein the urea melt of step (b) contains 95 to 98.8% wt.

13. The process according to claim 7, wherein the recovered urea solution has a urea concentration of 96% wt.

14. The process according to claim 9, wherein the temperature of the air stream after the heating stage is in the range of 130 to 140° C.

* * * * *